Figure 1:
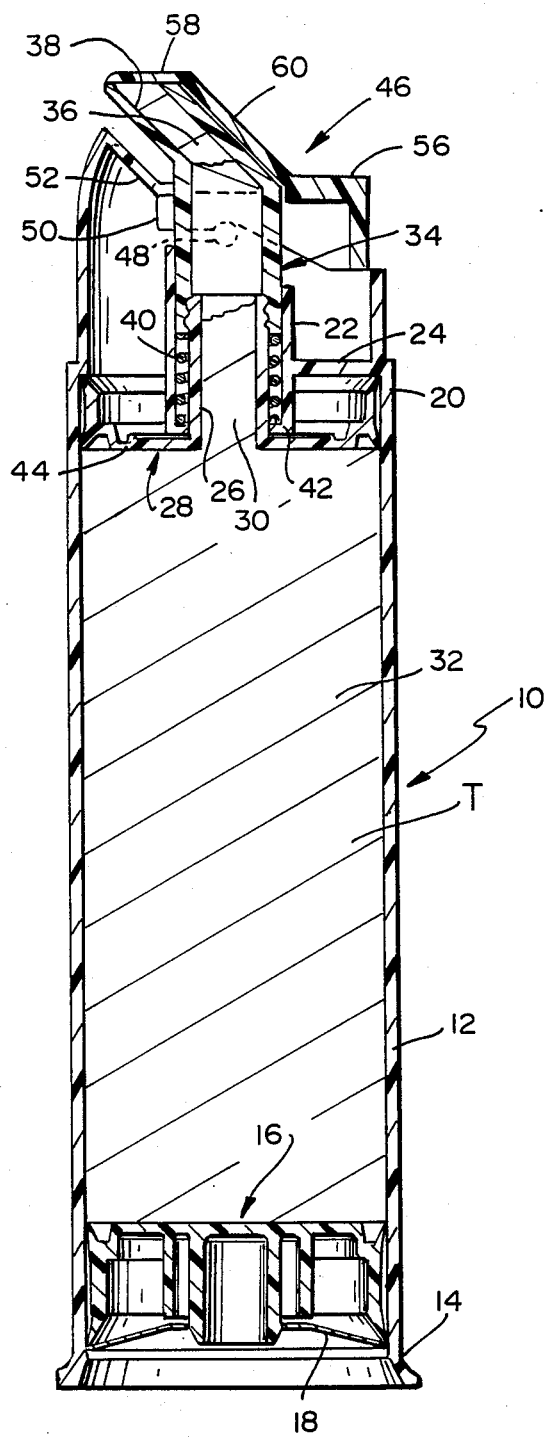

United States Patent [19]

Mazzanobile

[11] Patent Number: 4,830,221

[45] Date of Patent: May 16, 1989

[54] TOOTHPASTE PUMP FORMULATION

[75] Inventor: Salvatore Mazzanobile, Haworth, N.J.

[73] Assignee: Beecham Inc., Clifton, N.J.

[21] Appl. No.: 878,008

[22] Filed: Jun. 24, 1986

[51] Int. Cl.[4] .......................... A61K 7/26; B65D 35/00
[52] U.S. Cl. ........................................ 222/92; 424/49; 424/58; 222/260
[58] Field of Search ...................... 424/49, 58; 222/92, 222/153, 260, 386.5, 387, 498, 505

[56] References Cited

U.S. PATENT DOCUMENTS

| | | | |
|---|---|---|---|
| 3,475,533 | 10/1969 | Mayrand | 424/57 |
| 3,574,824 | 4/1971 | Echeandia et al. | 424/50 |
| 3,705,940 | 12/1972 | Kirchgassner | 424/49 |
| 3,885,028 | 5/1975 | Cella et al. | 424/52 |
| 4,292,304 | 9/1981 | Barels et al. | 424/52 |
| 4,421,527 | 12/1983 | Wason | 424/52 |
| 4,425,322 | 1/1984 | Harvey et al. | 424/52 |
| 4,533,069 | 8/1983 | Drobish | 222/209 |

FOREIGN PATENT DOCUMENTS 0075410 4/1985 Japan .
2152152 7/1985 United Kingdom .

*Primary Examiner*—Margaret Moskowitz
*Assistant Examiner*—F. T. Moezie
*Attorney, Agent, or Firm*—Jacobs & Jacobs

[57] ABSTRACT

A plastic toothpaste dispenser containing an aqueous toothpaste that includes a flavoring oil and a non-toxic oil in an amount effective to reduce the loss of the flavoring oil escaping through the plastic dispenser.

17 Claims, 1 Drawing Sheet

U.S. Patent     May 16, 1989     4,830,221

TOOTHPASTE PUMP FORMULATION

The present invention relates to toothpaste for a toothpaste pump dispenser, and more particularly to improvements in the storage stability of such toothpastes.

As is known, toothpaste commonly contains flavoring oils, such as oils of spearmint, wintergreen, peppermint and the like. While these flavoring oils are volatile, their use in toothpaste packaged in conventional tubes has not raised the problem of flavor loss during storage because the laminated structure of the tubes, e.g. a laminate of plastic and aluminum, prevents the volatile flavoring oil from escaping. The toothpaste pumps now in use are made of plastic and do not provide a barrier to the loss of flavoring. Such toothpaste pump dispensers are exemplified by U.S. Pat. No. 4,511,068 and published U.K. patent application Nos. 2,152,152A and 2,157,372A, all of which are incorporated herein by reference thereto. These dispensers have a cylindrical plastic nozzle of small diameter through which the toothpaste is dispensed, and a cylindrical plastic reservoir of much larger diameter in which the bulk of the toothpaste is stored. Since flavor loss is a function of the surface area of the mass of toothpaste, and since the ratio of surface area to volume varies inversely with the diameter of the cylindrical mass of toothpaste, flavor loss during storage would be expected to be most acute in the toothpaste contained in the small diameter dispensing nozzle. In fact, this is the case, and the loss of flavoring oils is most troublesome when the toothpaste is initially dispensed, e.g. during dispensing of the first few "ribbons" of toothpaste from the nozzle. In extreme cases, the loss of flavoring oil from the toothpaste in the dispensing nozzle may cause the nozzle to become plugged.

The present invention reduces the loss of flavoring oil in toothpaste stored in a plastic toothpaste dispenser by the incorporation herein of a non-toxic natural or synthetic oil in an amount effective to reduce the loss of flavoring oil as the toothpaste ages. In particular, the present invention provides a toothpaste dispenser having a plastic outlet nozzle and a plastic reservoir containing toothpaste, wherein the reservoir contains an extrudable, shape-retaining aqueous toothpaste, the aqueous toothpaste comprising an aqueous dental vehicle, a dental polishing or abrasive agent, from about 0.5 to about 2%, preferably from 0.5 to about 1.2% of flavoring oil, based on the total weight of the toothpaste, and from about 50 to about 150%, preferably from about 80 to about 120%, by weight, of a non-toxic oil, based on the weight of the flavoring oil. Preferably, the toothpaste dispenser is a pump dispenser having pumping means for dispensing toothpaste from the plastic reservoir and out of the outlet nozzle.

Figure 2:
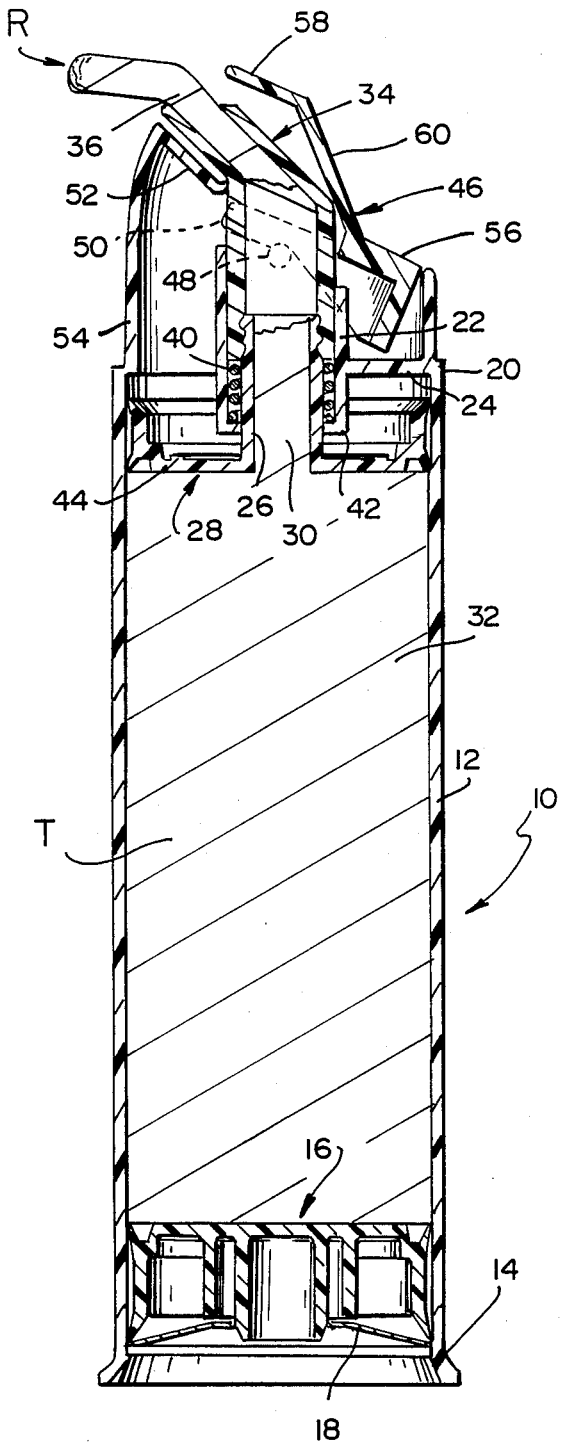

The present invention is illustrated in terms of a preferred embodiment in the accompanying drawing, wherein:

FIGS. 1 and 2 are elevational views, in section, of a pump dispenser in the closed and dispensing positions, respectively.

The toothpaste pump dispenser 10 of FIGS. 1 and 2 is filled with toothpaste T and includes a tubular, cylindrical body 12 which is open at its lower end 14 to the atmosphere, except for the presence of a floating piston 16 which makes sealing engagement with the interior wall surface of the body 12 and has a downwardly and outwardly flaring metal skirt 18 or the like on the bottom side thereof which also engages the interior wall surface of the body 12. The skirt 18 is sufficiently resilient that it will deflect downwardly to any extent necessary to permit the piston 16 to move upwardly in the body 12, yet it is sufficiently stiff as to bite into the wall surface and prevent downward, retrograde movement by the piston 16 within the body 12. The opposite, upper end 20 of the body 12 includes an upright, centrally disposed sleeve 22 which is supported by transversely extending web means 24. The sleeve 22 reciprocably receives the tubular stem 26 of a pumping piston 28 which at its circumferential periphery sealingly engages the inner wall surface of the body 12. A passage 30 is defined within the tubular stem 26, and the two pistons 16 and 28 cooperate with the body 12 to form a pumping chamber or reservoir 32 therebetween.

The sleeve 22 also partially receives the lower end of a tubular discharge spout or nozzle 34 which itself receives the upper end of the plunger stem 26 and is securely attached thereto. A passage 36 is defined within the tubular spout or nozzle 34, and a discharge outlet 38 is presented at the uppermost end thereof. A coil spring 40 encircles the piston stem 26 and is trapped between the lower extremity of the spout 34 and a lower, inturned terminus 42 of the sleeve 22 for the purpose of yieldably biasing the piston 28 and the spout 34 toward an upper, undepressed position as illustrated in FIG. 1 as limited by the lower sleeve terminus 42 abutting the inside of the pumping face 44 of piston 28.

The toothpaste dispenser 10 is also provided with an actuator 46 in the form of a lever having a fulcrum 48 associated with the spout 34. The fulcrum 48 takes the form of a pair of pins projecting laterally from opposite sides of the spout 34, and a pair of legs 50 of the actuator 46 (only one leg 50 being illustrated) straddle the spout 34 and rest at their midpoints on the respective fulcrum pins 48. Forwardmost ends of the legs 50 are retainingly hooked beneath overhanging proximal ledges 52 (only one being shown) on upstanding housing structure 54 at the upper end 20 of the body 12.

The actuator lever 46 includes a finger-engaging portion 56 on one side of the fulcrum pins 48, as well as a valve flap portion 58 on the opposite side of the fulcrum pins 48. The valve portion 58 is integrally connected with the finger-engaging portion 56 by an intermediate web portion 60, and it will be noted that the valve portion 58 is of such a dimension as to completely cover and thereby close the outlet 38 when the actuator 46 is in its FIG. 1 position. If desired, the spout 34 may have an angled upper end as shown in order to best accommodate the valve portion 58 and web portion 60 of actuating lever 46.

Dispenser 10 is filled with toothpaste T in a conventional manner. Thus, empty dispensers 10 without the floating piston 16 are sent to a toothpaste filling machine (not shown) with dispensers 10 in a inverted position. Toothpaste T is charged into the empty dispensers 10 and fills passage 36, then passage 30 and then the pumping chamber or reservoir 32. After completion of the filling operation, piston 16 is inserted to complete the assembly. The toothpaste filling apparatus may be any of the conventional machines used for filling toothpaste tubes. When a striped toothpaste is to be charged into the dispensers 10, such as a toothpaste having an opaque paste body with transparent or translucent gel stripes, then the filling apparatus of Evans British Patent No. 962,757 may be used, as is known.

The filled dispensers 10 are operated as follows. The return spring 40 normally maintains the pumping piston 28, the spout 34 and the actuator 46 in the position of FIG. 1 in which valve flap 58 tightly covers and seals the outlet 38. Upon the application of downwardly directed finger pressure to the operating portion 56 of actuator 46, the latter rocks downwardly about the fulcrum pins 48 in a clockwise direction so that the valve flap 58 is lifted off the outlet 38 as illustrated in FIG. 2. At the same time, because the legs 50 are retained beneath the ledges 52, depression of the operating portion 56 also causes the spout 34 and hence the pumping piston 28 to be shifted downwardly a short distance. This exerts a positive pumping pressure on the toothpaste contained within chamber 32 and forces the toothpaste upwardly through passages 30 and 36 and out the outlet 38. A ribbon R of toothpaste is thus dispensed.

When pressure on the operating portion 56 is released, the spring 40 returns the spout 34 to its original raised position of FIG. 1 and likewise forces the pumping piston 28 back to its original position. By virtue of the fulcrum pins 48 moving upwardly at this time and the legs 50 being trapped beneath the ledges 52, the actuator 46 is rocked in a counterclockwise direction about fulcrum pins 48 to thereby return the operating portion 56 to its original undepressed position and lower the valve flap 58 once again into covering relationship with the outlet 38. In view of the evacuation of product within the chamber 32 and the closing of the outlet 38 by valve flap 58, the floating piston 16 is moved upwardly within the chamber 32 by a corresponding amount as atmospheric pressure is applied against the bottom of the piston 16 via the open lower end 14 of the body 12.

As discussed above, loss of flavoring oils is most acute from the toothpaste in passage 36, particularly when the dispenser 10 is used to dispense the initial ribbons of toothpaste T, whereas toothpaste in the chamber or reservoir 32 experiences much less flavor loss during storage. It is believed that this difference in flavor loss is due to the fact that the ratio of surface area to volume is much higher for the toothpaste in the small diameter passage 6 than in the large diameter reservoir 32.

The dispenser 10 illustrated in the drawing is that of Realex Corporation's U.K. published patent application No. 2,152,152A, corresponding to U.S. Ser. No. 565,540, filed Dec. 27, 1983. The dispenser may also be that disclosed in Realex Corporation's published U.K. patent application No. 2,157,372A, corresponding to U.S. Ser. No. 589,640, filed Mar. 14, 1984. Furthermore, while the toothpaste dispenser is preferably in the form of a plastic pump, the present invention also contemplates the use of a plastic squeeze tube as the dispenser, wherein the reservoir and the outer nozzle are made of plastic without a metal barrier layer laminated thereto.

Plastic squeeze tubes useful in the present invention may be formed from polyolefins, such as polypropylene, by any suitable plastics fabrication technique, such as extrusion. Plastic toothpaste pumps are also formed from polyolefins, such as polypropylene, as by injection molding of the reservoir, piston etc. and assembly thereof Usefully, the non-toxic oil will be present in an amount effective to reduce flavor loss in the range of from about 0.25 to about 3%, such as from about 0.4 to about 2.4% by weight, based on the total weight of the toothpaste. However, when the amount of the oil exceeds about 1% by weight of the total weight of the composition, the taste of the toothpaste may become adversely affected unless suitable masking agents are used, and this, together with the increased cost of the use of larger amounts of oil, make it presently preferred to use from about 0.4 to about 1.5% by weight of the oil, based on the total weight of the composition. It is also presently preferred to use an amount of oil that is from about 80 to about 120%, preferably from about 90 to about 110%, by weight, based on the flavoring oil.

Suitable non-toxic oils for use in the present invention include petroleum or mineral or hydrocarbon oils derived from crude petroleum, such as mineral oil U.S.P. or light mineral oil N.F., and the like, oils derived from animal fats or vegetables, such as squalene oil, olive oil, corn oil and the like and synthetic oils such as fatty acid esters and ethoxylated esters, e.g. isopropyl myristrate oil, sorbitan monolaurate oil, ethoxy(20)sorbitan monolaurate and the like.

Mineral oil and light mineral oil are hydrocarbon oils derived from petroleum. USP XXI defines mineral oil as having a kinematic viscosity of not less than 34.5 centistokes at 40° C. and a specific gravity of 0.845–0.905 and NF XVI defines light mineral oil as having a kinematic viscosity of not more than 33.5 centistokes at 40° C. and a specific gravity of 0.818 to 0.880. It is presently preferred to use light mineral oil NF or an oil of similar viscosity and specific gravity, and most preferably a light mineral oil having a kinematic viscosity at 40° C. of from about 6.7 to about 9.7 centistokes and a specific gravity of from about 0.822 to about 0.833, or an oil of similar viscosity and specific gravity.

The toothpaste according to the invention may employ any desired flavoring oil or mixture thereof, such as those suitably employed in toothpaste, such as oils of spearmint, peppermint, wintergreen, sassafras, cinnamon, anise, clove, carraway, eucalyptus, thyme, menthol, lemon, orange, nutmeg, eugenol, L-carvone, anethol, coriander, ginger, casia, and vanillin and methyl salicylate. The specific flavoring oil employed is not critical, since the present invention is applicable to any of the flavoring oils. Generally, the flavoring oil will be employed in minor amounts, such as from about 0.5 to 2% by weight, based on the total weight of the toothpaste, and more usually from about 0.5 to about 1.2%.

In one embodiment of the invention, larger amounts of the flavoring oil and non-toxic oils are employed, namely from about 0.80 to about 1.5%, preferably from about 0.85 to about 1.0%, by weight of the flavoring oil, based on the total weight of the toothpaste, and from about 80 to about 120%, preferably from about 90 to about 110%, by weight of the non-toxic oil, based on the weight of the flavoring oil. Excellent results have been obtained using from about 0.85 to about 1.0% by weight of the flavoring oil, based on the total weight of the toothpaste, and about 100% by weight of the non-toxic oil, based on the weight of the flavoring oil.

In another embodiment of the invention, smaller amounts of the flavoring oil and non-toxic oil are employed, namely from about 0.55 to about 0.75%, preferably from about 0.60 to about 0.70%, by weight of the flavoring oil, based on the total weight of the toothpaste, and from about 80 to 120%, preferably from about 90 to about 110%, by weight of the non-toxic oil, based on the weight of the flavoring oil. Suitably, in this embodiment of the invention, from about 0.60 to about 0.70% by weight of the flavoring oil, based on the total weight of the toothpaste, and about 100% by weight of the non-toxic oil, based on the weight of the flavoring oil, will be used.

The toothpaste of the present invention will preferably contain a fluoride ion source sufficient to provide from about 50 to about 3500 ppm, most preferably from about 500 ppm to about 3000 ppm, of fluoride ions. Suitable fluoride ion sources include sodium fluoride, stannous fluoride, potassium fluoride, potassium stannous fluoride, stannous chlorofluoride, sodium monofluorophosphate, sodium fluorozirconate, potassium fluorozirconate, stannous fluorozirconate, indium fluorozirconate and complex zirconium-germanium fluorides, e.g. $Zr(GeF_6)_2$, $ZrGeF_8$, $Ge(ZrF_6)_2$ and $ZrO-GeF_6$. Other suitable fluoride ion sources include ammonium fluoride, indium fluoride, ferrous fluoride, lithium fluoride, fluorosilicates, such as $Na_2SiF_6$, calcium fluorozirconates, fluorostannites, such as $NaSnF_3$, fluoroborates, such as $NaBF_4$, fluorotitanates, such as $NaTiF_5$ and mixed tin fluorohalides, such as $SnClF$ and $Sn_2ClF_6$. Mixtures of fluoride ion sources may be used. The presently preferred fluoride ion sources are sodium fluoride and sodium monofluorophosphate or mixture thereof.

The toothpaste of the invention also comprises a dental polishing or abrasive agent such as calcium carbonate, water-insoluble sodium or potassium metaphosphates, hydrated or anhydrous dicalcium phosphate, calcium pyrophosphate, zirconium silicate, silica or mixtures thereof, in which case an opaque paste is generally obtained.

The toothpaste of the invention may also contain surfactants, gelling agents, and other excipients, such as coloring agents.

The surfactant is normally a water-soluble non-soap or synthetic organic detergent. Suitable surfactants include the water-soluble salts of higher fatty acid monoglyceride monosulphates (for example sodium hydrogenated coconut fatty acid monoglyceride monosulphate); higher alkyl sulphates (for example sodium lauryl sulphate); alkylarylsulphonates (for example, sodium dodecylbenzenesulphonate); and higher alkyl sulphoacetates (for example, sodium lauryl sulphoacetate). There may also be used the saturated higher aliphatic acyl amides of lower aliphatic amino carboxylic acids having 12 to 16 carbon atoms in the acyl radical and in which the amino acid portion is derived from the lower aliphatic saturated monoaminocarboxylic acids having 2 to 6 carbon atoms, such as the fatty acid amines of glycine, sarcosine, alanine, 3-aminopropanoic acid and valine, particularly the N-lauroyl, myristoyl and palmitoyl sarcosinate compounds. Conventional non-ionic surfactants may also be included if desired. Examples of suitable non-ionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

The surface-active materials may be present in an amount of from about 0.05 to about 10%, preferably from about 0.5 to about 5%, of the composition.

The toothpaste according to the invention is a gel or paste that may employ a gelling agent, binder or thickener to provide the desired rheological properties. Such agents are known in the art and include the natural and synthetic gums and gum-like materials, such as alkali metal carboxymethyl cellulose, hydroxyethyl carboxymethyl cellulose, polyvinyl pyrrolidone, Irish moss, gum tragacanth, hydroxypropyl methyl cellulose, methyl cellulose, starches, starch glycolates, polyvinyl alcohol, alginates, carob bean gums, and hydrophilic colloidal carboxyvinyl polymers, such as those sold under the trademarks Carbopol 934 and Carbopol 940, diatomaceous earths, bentonite and other natural clays (these also may function as polishing agents), proteinaceous materials, either animal- or vegetable-derived, and synthetic inorganic clays, such as the silicated clays sold under the trademarks Laponite CP and Laponite SP. Certain colloidal silicas such as the aerogels, Syloids 244 and 266 and Aerosil, and pyrogenic silica, sold as Cab-O-Sils, may be used also for thickening or gelling properties. Of course, as with the other constituents of the invention, mixtures thereof may be employed to obtain specially desirable properties in the product. It is presently preferred to use fumed silica or a cellulose gum as the binder or thickener.

The amount of gelling agent or thickener is sufficient to form an extrudable, shape-retaining product which can be dispensed from a pump dispenser onto a toothbrush and will not fall between the bristles of the brush but rather will substantially maintain its shape thereon. In almost all cases, no more than about 15% of gelling agent need be used and in most instances from 0.5 to about 15% will suffice.

The aqueous dental vehicle comprises a mixture of water and a humectant, such as glycerin, aqueous sorbitol, polyethylene glycol or propylene glycol. The total liquid content is generally in the range from about 20% to about 95%, and typically comprises up to about 40% of water, 0 to about 80% of glycerine, 0 to about 80% of sorbitol and 0 to 20% propylene glycol and/or polyethylene glycol. Preferably, 0 to about 40% of glycerine, 0 to about 60% of sorbitol, and 0 to 10% propylene glycol and/or polyethylene glycol are present. It is presently preferred to use aqueous sorbitol and/or liquid polyethylene glycol as the humectant. Polyethylene glycol has the formula $HO(CH_2CH_2O)_nH$, where n is an integer, such as from about 2 to about 40.

Other materials may be added, such as soluble saccharin, coloring or whitening agents (e.g. titanium dioxide), preservatives (e.g. sodium benxoate), emulsifying agents, silicones, alcohol, chlorophyll compounds (e.g. sodium copper chlorophyllin), and anti-bacterial agents (e.g. chlorhexidine). These materials, when present, will be in minor amounts, such as up to about 4%, e.g. from about 0.05 to about 3% in total.

A preferred composition for use in the present invention comprises

| | |
|---|---|
| 10 to 70% | humectant |
| 5 to 30% | deionized water |
| 2 to 40% | polishing agent |
| 0.5 to 15% | gelling agent, binder or thickener |
| 1 to 3% | surfactant |
| 0.4 to 1.5% | non-toxic oil |
| 0.5 to 1.2% | flavoring oil |
| 0.5 to 2% | sweetener and colorant |

The toothpaste of the invention is prepared in the usual manner by mixing the ingredients in the dry state or as slurries or solutions. The pH of the toothpaste will generally be from between about 3.5 and about 9.5.

The present invention is illustrated in terms of its preferred embodiments in the Examples that follow. In this specification and claims, all parts and percentages are by weight, unless otherwise stated.

EXAMPLE 1

A toothpaste according to the present invention was prepared and dispensed into toothpaste pump dispensers of FIGS. 1 and 2 in the form of a white paste body with aqua and red gel stripes. The composite formula of the toothpaste contained in the toothpaste pump was as follows:

|  | % |
| --- | --- |
| Polyethylene Glycol (400 Mw) | 3.0 |
| Sorbitol (70% aqueous solution) | 12.2 |
| Glycerine | 34.9 |
| Deionized Water | 11.9 |
| Carboxymethyl Cellulose | 0.6 |
| Calcium Carageenan | 0.1 |
| Silica Thickener | 0.1 |
| Calcium Carbonate | 17.8 |
| Hydrated Silica | 13.2 |
| Titanium dioxide | 1.0 |
| Flavoring Oils | 1.0 |
| Light Mineral Oil NF* | 1.0 |
| Sodium Lauryl Sulfate | 1.2 |
| Sodium Monofluorophosphate | 0.8 |
| Sodium Saccharin | 0.2 |
| Sodium Benzoate | 0.2 |
| Sodium Silicate | 0.2 |
| Colorants | 0.7 |
| Calcium Glycerophosphate | 0.1 |

*Viscosity: 6.7–9.7 centistokes at 40° C.
Specific gravity (25° C.): 0.822–0.833
Pour point: 7° C.
Flash Point: 138° C.

EXAMPLE 2

Following the procedure and using the ingredients of Example 1, a toothpaste was prepared containing 0.85% of flavoring oil and 0.85% of the light mineral oil, and the amount of glycerine was increased to 35.2%. Toothpaste pump dispensers were filled with the toothpaste of this Example.

EXAMPLE 3

By changing the colorants used in Example 1, two toothpastes were prepared having a white paste body and aqua gel stripes. In one toothpaste, the flavoring oils and the light mineral oil were each present in an amount of 0.60% and in the other they were each present in an amount of 0.70%. Toothpaste pump dispensers were filled with the toothpastes of this Example.

EXAMPLE 4

Storage stability tests were-conducted by storing toothpaste pump dispensers filled with the toothpaste of Examples 1 and 3 or a control for three months at room temperature or at 45° C. After storage, the toothpaste was dispensed from the pump and the amount of flavoring oil in each of the first five "ribbons" of toothpaste and in approximately the middle of the reservoir was determined. The results were as follows:

TABLE 1

Storage For Three Months At Room Temperature Flavoring Oil Retained As Percentage Of Initial Content Thereof

|  | TEST ONE | | TEST TWO | |
| --- | --- | --- | --- | --- |
|  | Example 1 | Control* | Example 3 | Control** |
| Ribbon | | | | |
| #1 | 69.3 | 49.4 | 61.7 | 42.4 |
| #2 | 70.3 | 42.4 | 71.7 | 47.5 |
| #3 | 80.2 | 55.3 | 76.7 | 66.1 |
| #4 | 86.1 | 63.5 | 78.3 | 69.5 |
| #5 | 87.1 | 69.4 | 81.7 | 72.9 |
| "Middle" | 98.0 | 92.9 | 95.0 | 91.2 |

*Control toothpaste contained 0.85% flavoring oils and no light mineral oil.
**The toothpaste according to Example 3 contained 0.60% each of the flavoring oils and light mineral oil, whereas the control contained 0.60% flavoring oils and no light mineral oil.

TABLE 2

Storage For Three Months at 45° C. Temperature Flavoring Oil Retained As Percentage Of Initial Content Thereof

|  | TEST ONE | | TEST TWO | |
| --- | --- | --- | --- | --- |
|  | Example 1 | Control* | Example 3 | Control** |
| Ribbon | | | | |
| #1 | 32.7 | 18.8 | 23.9 | 25.4 |
| #2 | 32.7 | 25.9 | 28.2 | 27.1 |
| #3 | 43.7 | 32.9 | 36.6 | 35.6 |
| #4 | 44.6 | 36.5 | 46.5 | 37.3 |
| #5 | 45.6 | 37.6 | 46.5 | 39.0 |
| "Middle" | 75.2 | 62.4 | 69.0 | 67.8 |

*Control toothpaste contained 0.85% flavoring oils and no light mineral oil.
**The toothpaste according to Example 3 contained 0.70% each of the flavoring oils and light mineral oil, whereas the control contained 0.60% flavoring oils and no light mineral oil.

I claim:

1. A plastic toothpaste dispenser, which comprises, in combination:
    a. a toothpaste dispenser having a plastic outlet nozzle and an elongated plastic reservoir means for storing toothpaste, said reservoir means being closed at one end and open at the other end, said outlet nozzle being in communication with the open end of said reservoir means, whereby toothpaste in said reservoir means is dispensed from said reservoir means and out of said outlet nozzle; said reservoir means and said outlet nozzle being made of plastic without a metal barrier layer laminated thereto; and
    b. an extrudable, shape-retaining aqueous toothpaste within said reservoir means and said outlet nozzle, comprising an aqueous dental vehicle, a dental polishing agent, from about 0.5 to about 2% by weight of a flavoring oil or a mixture of flavoring oils, based on the total weight of said toothpaste, and, in addition to said flavoring oil, from about 50 to about 150% by weight of a non-toxic oil, based on the weight of said flavoring oil.

2. Apparatus according to claim 1, wherein the amount of said non-toxic oil is from about 80 to about 120% by weight, based on the weight of said flavoring oil.

3. Apparatus according to claim 1, wherein the amount of said flavoring oil is from about 0.80 to about 1.5% by weight.

4. Apparatus according to claim 1, wherein the amount of said flavoring oil is from about 0.55 to about 0.75% by weight.

5. A plastic toothpaste dispenser, which comprises, in combination:
   a. a toothpaste dispenser having a plastic outlet nozzle and an elongated plastic reservoir means for storing toothpaste, said reservoir means being closed at one end and open at the other end, said outlet nozzle being in communication with the open end of said reservoir means, whereby toothpaste in said reservoir means is dispensed from said reservoir means and out of said outlet nozzle; said reservoir means and said outlet nozzle being made of plastic without a metal barrier layer laminated thereto; and
   b. an extrudable, shape-retaining aqueous toothpaste within said reservoir means and said outlet nozzle, comprising an aqueous dental vehicle, a dental polishing agent, from about 0.5 to about 2% by weight of a flavoring oil or a mixture of flavoring oils, based on the total weight of said toothpaste, and from about 50 to about 150% by weight of a non-toxic oil selected from the group consisting of mineral oil or light mineral oil, based on the weight of said flavoring oil.

6. Apparatus according to claim 5, wherein the amount of said flavoring oil is from about 0.80 to about 1.5% by weight and the amount of said non-toxic oil is from about 80 to about 120% by weight, based on the weight of said flavoring oil.

7. Apparatus according to claim 5, wherein the amount of said flavoring oil is from about 0.55 to about 0.75% by weight, and the amount of said non-toxic oil is from about 80 to about 120% by weight, based on the weight of said flavoring oil.

8. A plastic toothpaste pump dispenser, which comprises, in combination:
   a. a toothpaste pump dispenser having a plastic outlet nozzle, an elongated plastic reservoir means for storing toothpaste, said reservoir means being closed at one end and open at the other end, said outlet nozzle being in communication with the open end of said reservoir means, and pumping means for pumping toothpaste from said reservoir means and out of said outlet nozzle; said reservoir means and said nozzle being made of plastic without a metal barrier layer laminated thereto; and
   b. an extrudable, shape-retaining aqueous toothpaste within said reservoir means and said outlet nozzle, comprising an aqueous dental vehicle, a dental polishing or abrasive agent, from about 0.5 to about 2% by weight of a flavoring oil or mixture thereof, based on the total weight of said toothpaste, and, in addition to said flavoring oil, from about 50 to about 150% by weight of a non-toxic oil, based on the weight of said flavoring oil.

9. Apparatus according to claim 8, wherein the amount of said non-toxic oil is formed from about 80 to about 120% by weight, based on the weight of said flavoring oil.

10. Apparatus according to claim 8, wherein the amount of said flavoring oil is from about 0.80 to about 1.5% by weight.

11. Apparatus according to claim 8, wherein the amount of said flavoring oil is from about 0.55 to about 0.75% by weight.

12. A plastic toothpaste pump dispenser, which comprises, in combination:
   a. a toothpaste pump dispenser having a plastic outlet nozzle, an elongated plastic reservoir means for storing toothpaste, said reservoir means being closed at one end and open at the other end, said outlet nozzle being in communication with the open end of said reservoir means, and pumping means for pumping toothpaste from said reservoir means and out of said outlet nozzle; said reservoir means and said outlet nozzle being made of plastic without a metal barrier layer laminated thereto; and
   b. An extrudable, shape-retaining aqueous toothpaste within said reservoir means and said outlet nozzle, comprising an aqueous dental vehicle, a dental polishing or abrasive agent, from about 0.5 to about 2% by weight of a flavoring oil or mixture thereof, based on the total weight of said toothpaste, and from about 50 to about 150% by weight of a non-toxic oil selected from the group consisting of mineral oil or light mineral oil, based on the weight of said flavoring oil.

13. Apparatus according to claim 12, wherein the amount of said flavoring oil is from about 0.80 to about 1.5% by weight and the amount of said non-toxic oil is from about 80 to about 120% by weight, based on the weight of said flavoring oil.

14. Apparatus according to claim 13, wherein the amount of said flavoring oil is from about 0.55 to about 0.75% by weight and the amount of said non-toxic oil is from about 80 to about 120% by weight, based on the weight of said flavoring oil.

15. Apparatus according to claim 12, wherein said non-toxic oil is light mineral oil.

16. Apparatus according to claim 13, wherein said non-toxic oil is light mineral oil.

17. Apparatus according to claim 14, wherein said non-toxic oil is light mineral oil.

* * * * *